United States Patent
Kim et al.

(10) Patent No.: US 9,577,400 B2
(45) Date of Patent: Feb. 21, 2017

(54) FREQUENCY SHIFTING OPTICAL SWEPT LIGHTSOURCE SYSTEM AND APPARATUS TO WHICH THE SYSTEM IS APPLIED

(71) Applicants: SAMSUNG ELECTRONICS CO., LTD., Suwon-si (KR); Seoul National University R&DB Foundation, Seoul (KR)

(72) Inventors: Hong-sig Kim, Seongnam-si (KR); Yoon-chan Jeong, Seoul (KR); Young-chul Kwon, Seoul (KR); Luis Alonso Vazquez Zuniga, Seoul (KR); Woo-young Jang, Seongnam-si (KR)

(73) Assignees: SAMSUNG ELECTRONICS CO., LTD., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 455 days.

(21) Appl. No.: 14/218,059

(22) Filed: Mar. 18, 2014

(65) Prior Publication Data
US 2016/0172815 A1   Jun. 16, 2016

(30) Foreign Application Priority Data
Mar. 18, 2013   (KR) .................. 10-2013-0028425

(51) Int. Cl.
*H01S 3/00* (2006.01)
*G02F 1/35* (2006.01)
(Continued)

(52) U.S. Cl.
CPC ......... *H01S 3/0092* (2013.01); *G01B 9/02091* (2013.01); *G02F 1/353* (2013.01);
(Continued)

(58) Field of Classification Search
None
See application file for complete search history.

(56) References Cited

U.S. PATENT DOCUMENTS 5,880,877 A    3/1999 Fermann et al.
6,509,993 B1   1/2003 Gnauck et al.
(Continued)

FOREIGN PATENT DOCUMENTS

EP   1617278 A1   1/2006
JP   2008-209342 A   9/2008
(Continued)

OTHER PUBLICATIONS

Communications dated May 29, 2014 issued by the International Searching Authority in counterpart International Application No. PCT/KR2014/002287 (PCT/ISA210 * PCT/ISA/237).
(Continued)

*Primary Examiner* — Hemang Sanghavi
(74) *Attorney, Agent, or Firm* — Sughrue Mion, PLLC

(57) ABSTRACT

Provided is a frequency shifting optical swept light source system. The system includes a light source that emits light; an amplifier that amplifies the light output from the light source; an optical converter that shifts a frequency of the amplified light and compresses a spectrum of the amplified light; and a controller that controls a current signal applied to the light source such that a repetition rate of the light output from the light source is adjusted, so that an intensity of the amplified light is adjusted, to thereby adjust a position of the compressed spectrum with respect to a predetermined frequency band.

20 Claims, 16 Drawing Sheets

(51) Int. Cl.
  *H01S 3/30* (2006.01)
  *H01S 3/10* (2006.01)
  *G01B 9/02* (2006.01)
  *G02F 1/365* (2006.01)
  *H01S 3/23* (2006.01)
  *H01S 3/067* (2006.01)
  *H01S 3/16* (2006.01)
  *A61B 3/10* (2006.01)
  *A61B 5/00* (2006.01)

(52) U.S. Cl.
  CPC ............ *G02F 1/3513* (2013.01); *G02F 1/365* (2013.01); *H01S 3/0057* (2013.01); *H01S 3/0078* (2013.01); *H01S 3/0085* (2013.01); *H01S 3/06754* (2013.01); *H01S 3/10046* (2013.01); *H01S 3/302* (2013.01); *A61B 3/102* (2013.01); *A61B 5/0066* (2013.01); *H01S 3/06758* (2013.01); *H01S 3/1618* (2013.01); *H01S 3/2308* (2013.01)

(56) References Cited

U.S. PATENT DOCUMENTS

| | | | |
|---|---|---|---|
| 7,733,922 | B1 | 6/2010 | Munroe et al. |
| 2003/0012492 | A1 | 1/2003 | Tadakuma et al. |
| 2005/0225846 | A1* | 10/2005 | Nati .................... H01S 3/06758 359/341.1 |
| 2006/0120418 | A1* | 6/2006 | Harter .................. H01S 3/0092 372/30 |
| 2006/0245703 | A1 | 11/2006 | Okuno |
| 2007/0025728 | A1 | 2/2007 | Nakazawa et al. |
| 2007/0160091 | A1 | 7/2007 | Lee et al. |
| 2008/0013163 | A1* | 1/2008 | Leonardo ................ G02F 1/353 359/341.31 |
| 2009/0244547 | A1 | 10/2009 | Ozawa |
| 2009/0244695 | A1 | 10/2009 | Marcinkevicius et al. |
| 2011/0002691 | A1* | 1/2011 | Lin ..................... H01S 3/10023 398/118 |
| 2013/0107351 | A1 | 5/2013 | Clowes et al. |

FOREIGN PATENT DOCUMENTS

| | | |
|---|---|---|
| KR | 10-2005-0114660 A | 12/2005 |
| KR | 10-1155541 B1 | 6/2012 |
| WO | 2009/095023 A2 | 8/2009 |

OTHER PUBLICATIONS

Mitschke, et al.; "Discovery of the Soliton Self-Frequency Shift", Optics Letters, Oct. 1986, vol. 11, No. 10, 3 pages total.

Gordon, "Theory of the Soliton Self-Frequency Shift", Optics Letters, Oct. 1986, vol. 11, No. 10, 3 pages total.

Communication dated Feb. 12, 2015, issued by the European Patent Office in counterpart European Application No. 14160448.8.

* cited by examiner

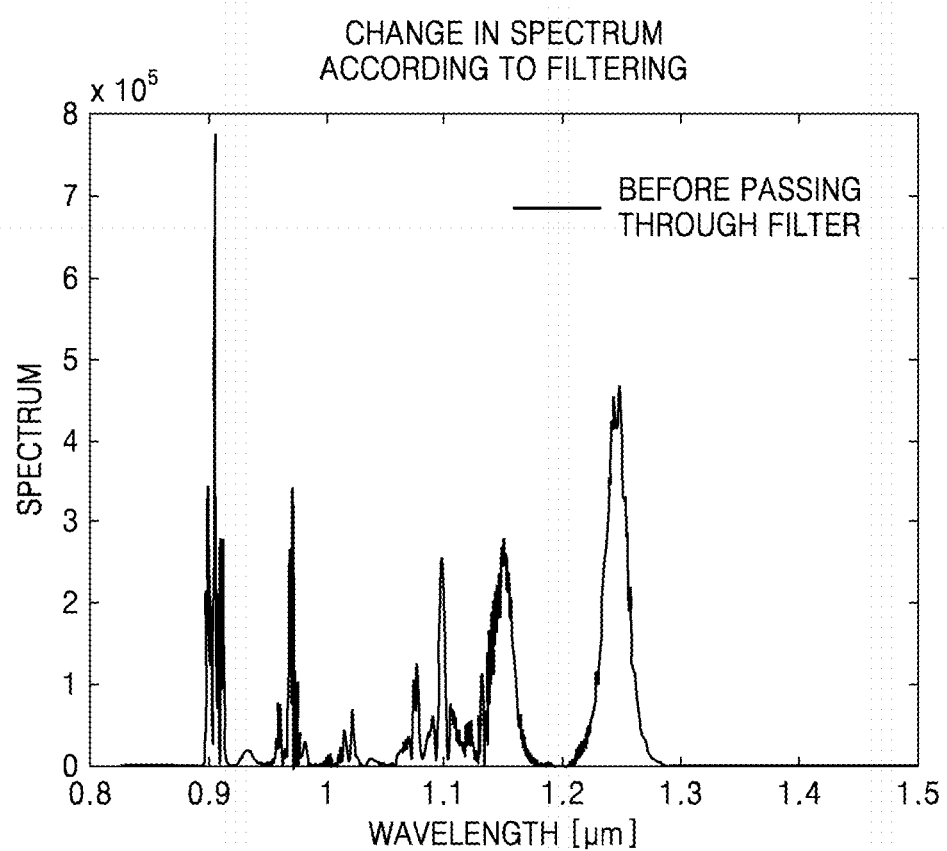

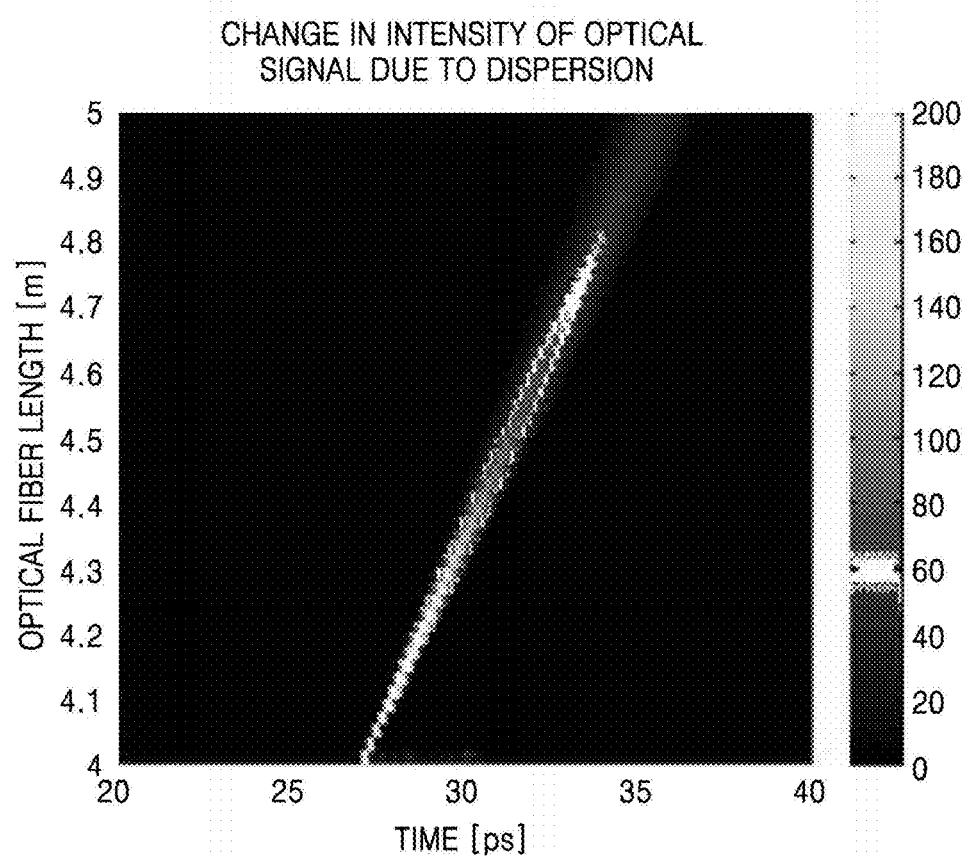

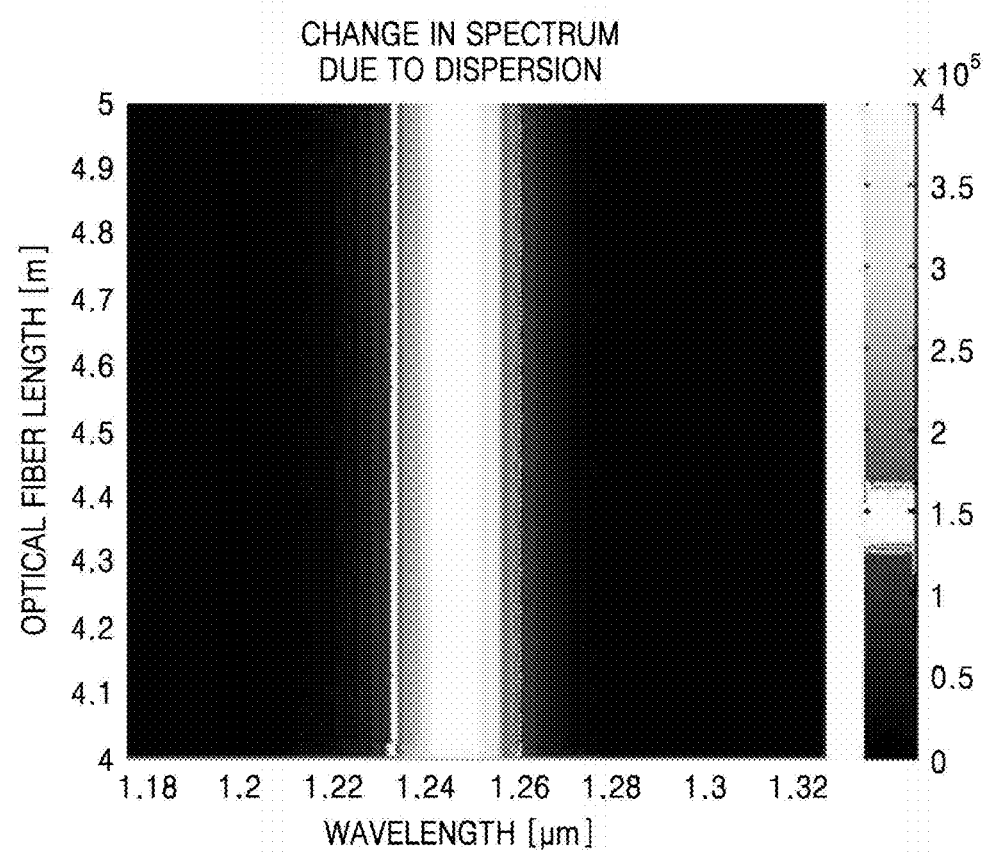

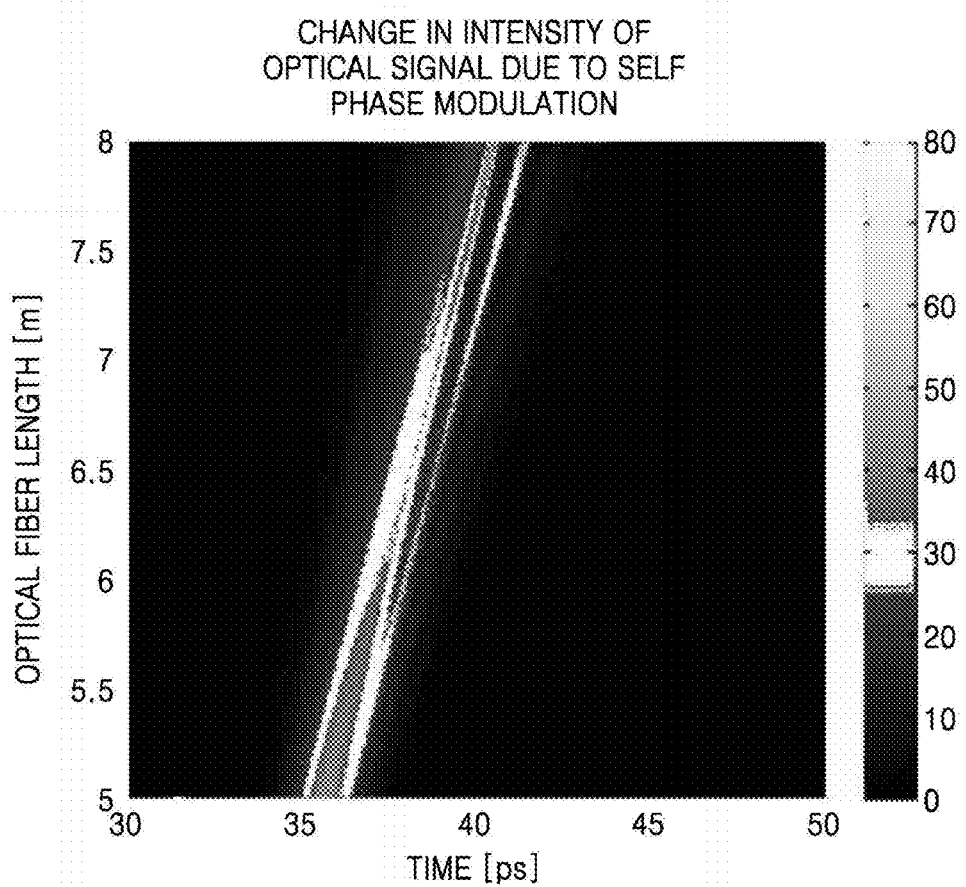

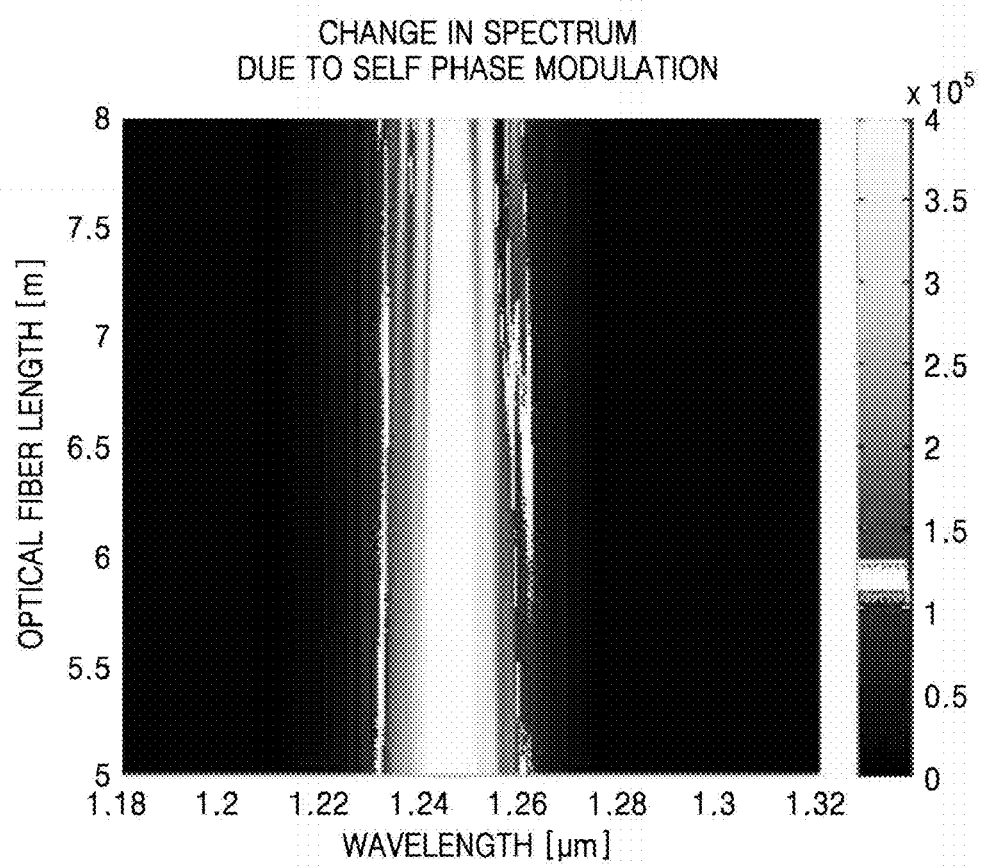

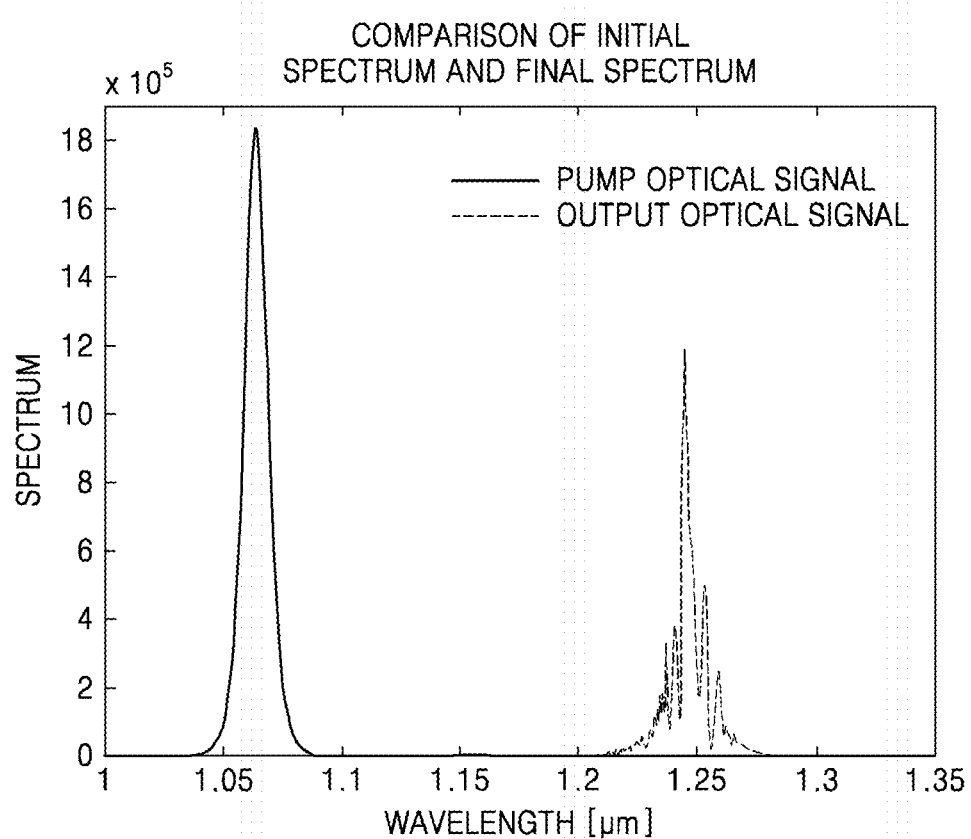

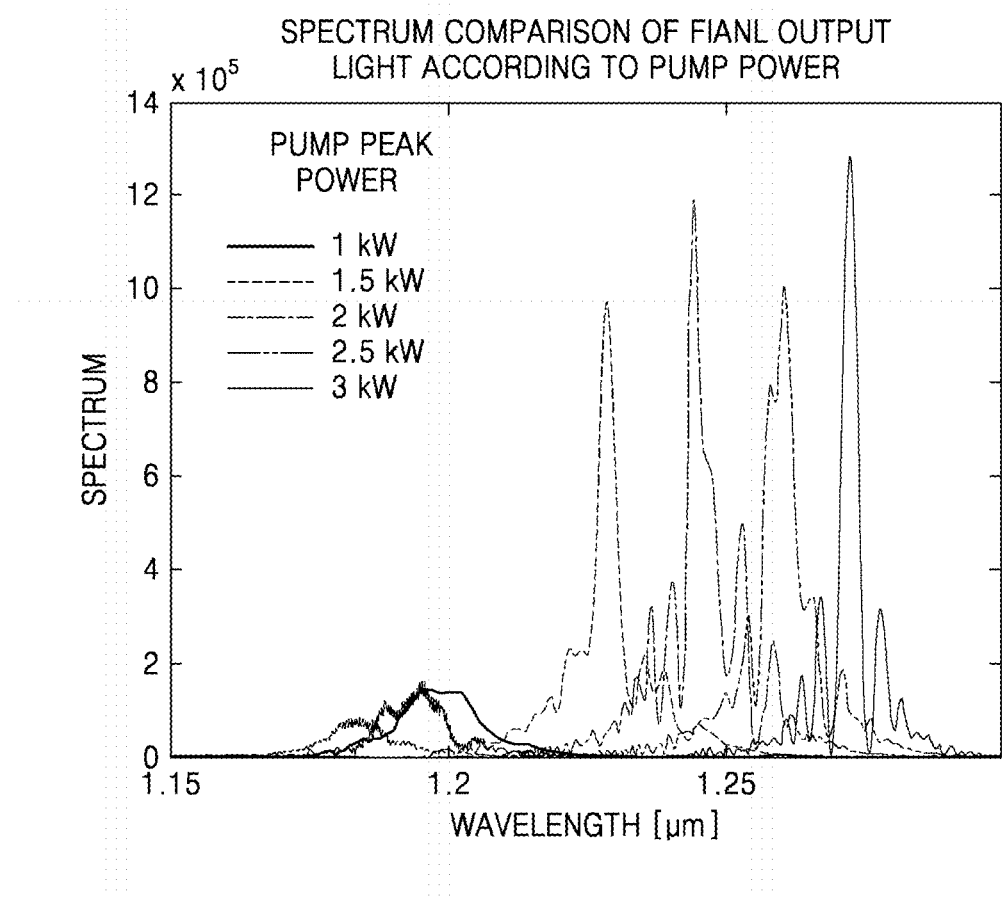

FREQUENCY SHIFTING OPTICAL SWEPT LIGHTSOURCE SYSTEM AND APPARATUS TO WHICH THE SYSTEM IS APPLIED

CROSS-REFERENCE TO RELATED APPLICATIONS

This application claims priority from Korean Patent Application No. 10-2013-0028425, filed on Mar. 18, 2013, in the Korean Intellectual Property Office, the disclosure of which is incorporated herein by reference in its entirety.

BACKGROUND

1. Field

Exemplary embodiments relate to light source systems and apparatuses to which the light source systems are applied, and more particularly, to frequency shifting optical swept light source systems and apparatuses to which the frequency shifting optical swept light source systems are applied.

2. Description of the Related Art

Laser light having monochromaticity, coherence, and directionality is used in various applications. In fields such as biotechnology and medicine, laser light is widely used for observing tissues and cells, diagnosing diseases, and/or providing laser treatments.

In particular, in medicine, an internal structure of a human body may be observed without directly making an incision in the human body when using and applying characteristics of laser light, and thus, causes and locations of various diseases and processes thereof may be detected easily and stably. As the laser light source technology continues to develop, light transmittance depth continues to improve, and thus, laser light is also applicable to fields in which tomographic images of living tissues and/or cells are obtainable in real time.

An operating wavelength band of a conventional optical fiber laser that is currently typically used may be limited, for example, to approximately 800 nm, approximately 1.06 μm, or approximately 1.55 μm, depending mainly on doped rare-earth elements used in the optical fiber laser. In order to use an optical fiber laser in fields for which wavelengths other than a radiation wavelength of a rare-earth element is necessary, a light source system which implements a frequency shift is being developed.

SUMMARY

Provided are frequency shifting optical swept light source systems which may be used as a light source for wavelengths other than a radiation wavelength of a rare-earth element, and apparatuses to which the systems are applied.

Additional aspects will be set forth in part in the description which follows and, in part, will be apparent from the description, or may be learned by practice of the presented exemplary embodiments.

According to an aspect of one or more exemplary embodiments, a frequency shifting optical swept light source system includes: a light source configured to emit light; an amplifier configured to amplify the light output from the light source; an optical converter configured to shift a frequency of the amplified light and to compress a spectrum of the amplified light; and a controller configured to control a current signal which is applied to the light source such that a repetition rate of the light output from the light source is adjusted, so that an intensity of the amplified light is adjusted, in order to thereby adjust a position of the compressed spectrum with respect to a first predetermined frequency band.

The optical converter may include: a frequency shifter configured to shift a first wavelength range of a band of the amplified light to a second wavelength range; a second-order disperser configured to disperse light processed by the frequency shifter, on a time axis; and a self phase modulator configured to compress a spectrum of the light received from the second-order disperser.

The frequency shifter may include a negative dispersion high-nonlinear optical fiber.

The second-order disperser may include a negative dispersion low-nonlinear optical fiber.

The self phase modulator may include a low-dispersion high-nonlinear optical fiber.

The optical converter may further include a filter that is disposed between the frequency shifter and the second-order disperser or between the second-order disperser and the self phase modulator, the filter being configured to pass a second predetermined frequency band.

The filter may include an optical fiber grating configured to function as a band pass filter with respect to a predetermined frequency component.

The optical converter may include: a soliton self-frequency shifter configured to perform frequency shifting in a soliton state, such that a first wavelength range of a band of the amplified light is shifted to a second wavelength range; a second-order disperser configured to disperse a soliton component which is incident from the soliton self-frequency shifter on a time axis and to apply negative chirping to the soliton component; and a self phase modulator configured to offset a portion of the negative chirping applied by using the second-order disperser, via self phase modulation, so as to cause spectrum compression with respect to the frequency band for which the portion of the negative chirping is offset, in a frequency domain.

The amplifier may be structured to perform at least a double amplification.

According to another aspect of one or more exemplary embodiments, an optical coherence tomography apparatus includes: a broadband swept light source system configured to implement the frequency shifting optical swept light source system described above; an interference optical system configured to separate light which is output from the light source system into measurement light and reference light, to irradiate the measurement light toward an object, and to cause an interference between light reflected by the object and the reference light in order to detect an interference signal; and an image signal processor configured to generate a tomographic image of the object by using the detected interference signal.

BRIEF DESCRIPTION OF THE DRAWINGS

These and/or other aspects will become apparent and more readily appreciated from the following description of exemplary embodiments, taken in conjunction with the accompanying drawings of which:

FIGS. 6A and 6B respectively illustrate output light shown in FIG. 2 before and after passing through a filter;

FIGS. 7, 8, 9A, and 9B illustrate variations in an intensity and a spectrum of light and chirping with time, while a soliton component illustrated in FIGS. 6A and 6B passes through an optical fiber that has a low non-linear coefficient and a negative dispersion coefficient;

FIGS. 10, 11, 12A, and 12B illustrate variations in an intensity and a spectrum of light and chirping with time due to self phase modulation while passing through an optical fiber that satisfies the condition of Inequality 6 below;

FIG. 13 illustrates a compressed spectrum which results from shifting seed light input into an optical converting unit of a light source system to a long wavelength band, according to an exemplary embodiment;

FIG. 14 illustrates swept light that is output when adjusting a repetition rate in a frequency shifting optical swept light source system, according to an exemplary embodiment.

DETAILED DESCRIPTION

Figure 1:
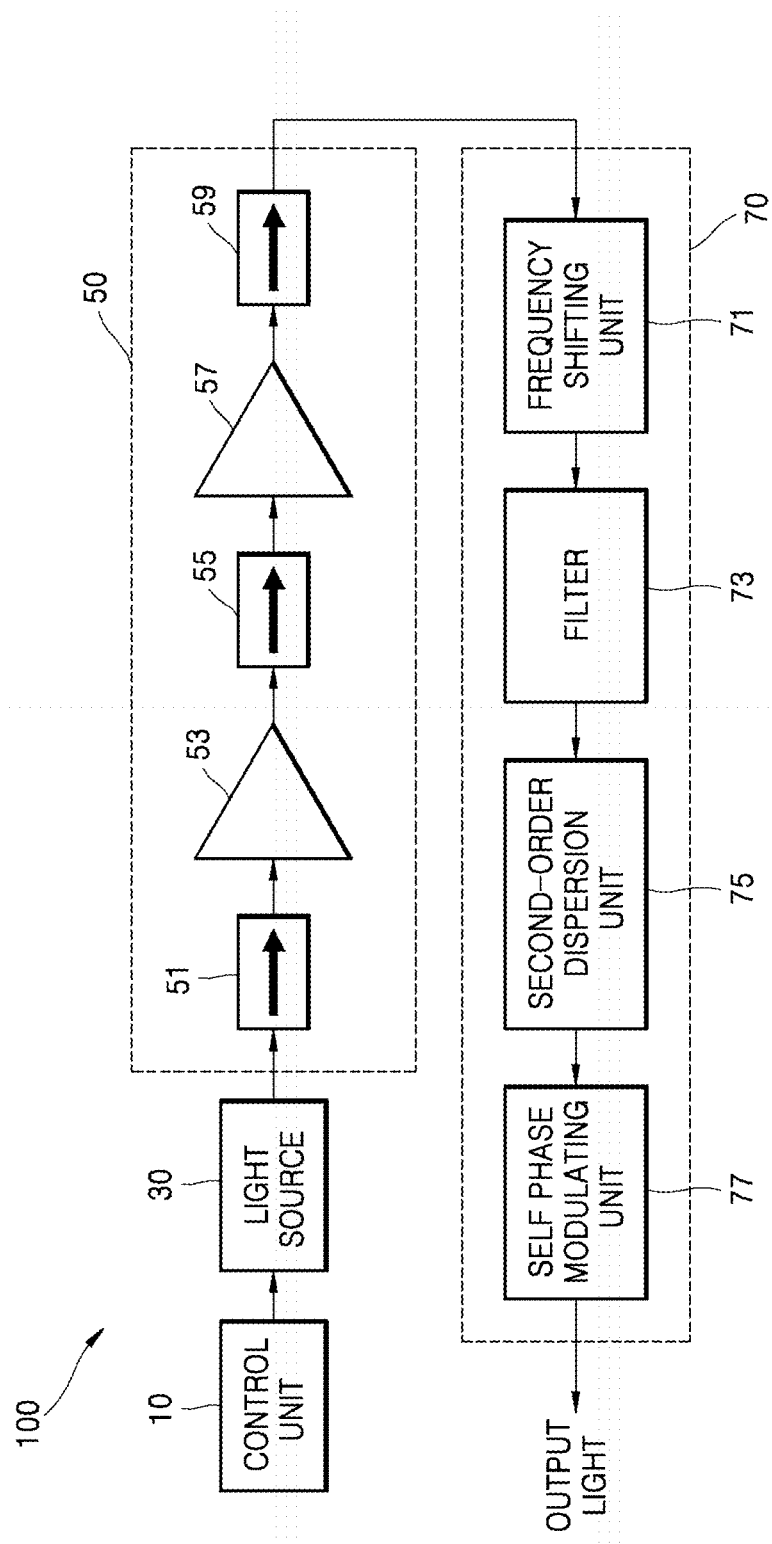
FIG. 1 is a schematic block diagram which illustrates a frequency shifting optical swept light source system, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure.

FIG. 1 is a schematic block diagram which illustrates a frequency shifting optical swept light source system 100, according to an exemplary embodiment.

Referring to FIG. 1, the frequency shifting optical swept light source system 100 includes a light source 30 that outputs light, an amplification unit (also referred to herein as an "amplifier") 50 that amplifies the light output from the light source 30, an optical converting unit (also referred to herein as an "optical converter") 70 that shifts a frequency of the light which is amplified by using the amplification unit 50 and compresses a spectrum of the amplified light, and a control unit (also referred to herein as a "controller") 10 that controls a current signal which is applied to the light source 30 such that a repetition rate of the light output from the light source 30 is adjusted. As a result of an application of the frequency shifting optical swept light source system 100, an intensity of the light that is amplified in and output from the amplification unit 50 is adjustable based on control of the control unit 10 so as to adjust a position of the compressed spectrum to with respect to a predetermined frequency band that is set for the light, wherein the frequency of the light is shifted and the spectrum of the light is compressed by using the optical converting unit 70. Consequently, a wavelength of light having a relatively narrow wavelength at a full width at half maximum (FWHM) may be instantaneously varied within a predetermined range to form broadband light for a predetermined period of time, thereby implementing a broadband swept light source.

The light source 30 may be provided to output laser light in the form of a pulse. The laser light which is output from the light source 30 may include, for example, seed light and/or pumping light, and a repetition rate of the light which is output from the light source 30 may be adjusted by adjusting a current which is applied based on a control of the control unit 10. Hereinafter, the light which is output from the light source 30 will be referred to as "seed light" for convenience, so that it may be easily distinguished from light amplified by using the amplification unit 50 and light that is transformed by using the optical converting unit 70.

The light source 30 may be provided to output seed light which has a central wavelength of about 1.064 μm, in the form of a pulse. In this case, as will be described later, when the amplification unit 50 uses Ytterbium-doped fiber (YDF), the amplification unit 50 may output light that is amplified to a band of about 1.064 μm.

The amplification unit 50 may be structured to perform at least a double amplification in order to obtain a high gain ratio. For example, the amplification unit 50 may include a plurality of amplifiers 53 and 57, and may further include a plurality of isolators 51, 55, and 59 at the front and back of the amplifiers 53 and 57 in order to prevent propagation of back-scattered light. The amplification unit 50 of FIG. 1 includes two amplifiers 53 and 57 and three isolators 51, 55, and 59, but the structure of the amplification unit 50 is not limited thereto and may vary. For example, the amplification unit 50 may have a triple amplification structure or a higher multiple amplification structure, and may include a corresponding plurality of isolators.

The amplification unit 50 may include an optical fiber laser, and a wavelength of light amplified by using the amplification unit 50 described above may vary based on a rare-earth element which is doped and which is used in the amplifiers 53 and 57.

For example, the amplifiers 53 and 57 may use YDF. In this case, the amplification unit 50 may amplify seed light that is input thereto by using the plurality of amplifiers 53 and 57 which are arranged in at least a double amplification structure, and may output amplified light which corresponds to a band of, for example, about 1.064 μm.

Further, energy which is input to the amplification unit 50 may be varied by adjusting any one or more of peak power of the seed light, pulse duration of the seed light, and a repetition rate of the seed light. In particular, a gain ratio of the amplification unit 50 may vary based on a repetition rate of input seed light. This may be understood as amplification being performed at a lower magnitude as a repetition rate (of light) increases, and thus a limited amount of energy being provided by the amplification unit 50 is distributed to more pulses of light per unit time. Accordingly, by adjusting a repetition rate of input seed light, an intensity of light amplified by and output from the amplification unit 50 may be adjusted. The light amplified by using the amplification unit 50 is transferred to the optical converting unit 70.

The optical converting unit 70 shifts a frequency of the light amplified by using the amplification unit 50 and compresses a spectrum of the amplified light, and includes a frequency shifting unit (also referred to herein as a "frequency shifter") 71 that shifts a first wavelength range of a band of the amplified light to a second wavelength range which corresponds to a longer wavelength band, a second-order dispersion unit (also referred to herein as a "second-order disperser") 75 that disperses the light processed by the frequency shifting unit 71 on a time axis, and a self phase modulating unit (also referred to herein as a "self phase modulator") 77 that compresses a spectrum of the light which is received from the second-order dispersion unit 75. The optical converting unit 70 may further include a filter 73. The optical converting unit 70 may include an optical fiber connecting portion. In particular, the frequency shifting unit 71, the filter 73, the second-order dispersion unit and the self phase modulating unit 77 may each be formed of an optical fiber, and may be optically connected to one another.

The frequency shifting unit 71 may be provided such that soliton self-frequency shifting is performed by Raman scattering. In particular, the frequency shifting unit 71 may include a soliton self-frequency shifting unit (also referred to herein as a "soliton self-frequency shifter") that shifts a band of light which corresponds to a first wavelength and which is output from the amplification unit 50 to a longer wavelength band, in a soliton state in which a shape of the light is maintained without any change. For example, the soliton self-frequency shifting unit 71 may use a negative dispersion high non-linear optical fiber. A degree of frequency shift is determined by a light intensity, and thus, a variation in a light intensity due to adjustment of a repetition rate conducted by using the amplification unit 50 may result in a position variation of the spectrum of the light.

The frequency-shifted light, which includes the soliton component and which occupies a relatively wide wavelength band, is filtered by using the filter 73, and as a result, only a corresponding frequency band component of the light which includes the soliton remains in the filtered light.

The filter 73 is designed to pass through only peripheral frequency bands which include the soliton component, and may be disposed between the frequency shifting unit 71 and the second-order dispersion unit 75, or between the second-order dispersion unit 75 and the self phase modulating unit 77. The filter 73 may include, for example, an optical fiber grating that functions as a band pass filter with respect to a predetermined frequency component. An optical fiber grating is formed by combining an optical fiber with a lattice whose refractive index varies periodically, and may function as a band pass filter with respect to a predetermined frequency component which corresponds to intervals and a distribution of refractive indices of the lattice.

In a phase modulating operation which is executable by using the self phase modulating unit 77, which will be described below, in general, even when the filter 73 is not included, or when the filter 73 is positioned at an end of the optical converting unit 70, a compressed spectrum may be obtained at a target wavelength band. However, a frequency component of a wavelength band lower than a zero dispersion wavelength may cause cross-phase modulation in a soliton component. When the filter 73 is disposed in front of the self phase modulating unit 77, cross phase modulation in a soliton component during phase modulation may be prevented. In this aspect, when a pass bandwidth of the filter 73 corresponds to a narrower bandwidth, a correspondingly greater amount of remaining light component other than a soliton is blocked, but a bandwidth of a final swept light is also limited. Thus, the pass bandwidth of the filter 73 should be set to an appropriate value in consideration of these characteristics. A soliton which remains after passing through the filter 73 is a transform-limited pulse without chirping.

The second-order dispersion unit 75 may impose dispersion, such as, for example, group velocity dispersion, to the soliton component that has passed through the filter 73 on the time axis; and may intentionally apply negative chirping to the soliton.

To this end, the second-order dispersion unit 75 may use a negative dispersion low-nonlinear optical fiber. By using the negative dispersion low-nonlinear optical fiber, when a dispersion coefficient is a negative number in a wavelength band in which a soliton is located, a spectrum of light is maintained almost uniformly, but an intensity of light is dispersed on a time axis, and negative chirping may be applied.

The self phase modulating unit 77 is included in order to compress a spectrum of light which is received from the second-order dispersion unit 75, and a portion of negative chirping which is applied due to dispersion may be offset by this self phase modulation. This causes compression of a spectrum with respect to a frequency band for which chirping is offset in a frequency domain. Accordingly, unlike in the second-order dispersion operation, the self phase modulating unit 77 may use a low-dispersion high-nonlinear optical fiber which has a high-nonlinear coefficient and a low dispersion coefficient in a corresponding frequency band, in order to vary via mainly self phase modulation.

Phenomena that may cause a variation in an optical signal in the optical converting unit 70 as described above will be described below in detail.

Second-order dispersion is a phenomenon by which light is dispersed on a time axis due to different speeds of various frequency components of the light. As a result, a frequency of light which is dispersed on a time axis is aligned based on speed, and this alignment is referred to as frequency chirping.

A length of an optical fiber that is required in order to allow significant second-order dispersion is referred to as a dispersion length, which depends on a width of an optical signal and a dispersion coefficient of an optical fiber. The dispersion length may be expressed in a numerical formula, as indicated in Equation 1 below.

[Equation 1]

$$L_D = \frac{T_0^2}{|\beta_2|} \quad (1)$$

where $L_D$ denotes a dispersion length, $\beta_2$ denotes a dispersion coefficient of an optical fiber, and $T_0$ denotes an initial FWHM value of an optical signal. As can be seen in Equation 1, a dispersion length is relatively short when a dispersion coefficient is relatively large and a width of an optical signal is relatively small. In general, a dispersion coefficient will have a value which corresponds to several tens of $ps^2/km$, and in order to obtain a dispersion length of less than a level of one km, a FWHM value of a pulse must be at a level of several ps or several fs.

Further, self-phase modulation is based on an optical Kerr effect by which a refractive index of an optical fiber varies in proportion to light intensity, and a phase that is proportional to light intensity is applied. Self phase modulation includes applying positive chirping to a center portion of an optical fiber with a high light intensity, and causes dispersion in a spectrum of an optical signal in a frequency domain, unlike the second-order dispersion. A length of an optical fiber which is required in order to allow significant self-phase modulation is referred to as a nonlinear length, which depends on the intensity of an optical signal and a nonlinear coefficient of an optical fiber. The nonlinear length may be expressed in a numeral formula, as indicated in Equation 2 below.

[Equation 2]

$$L_{NL} = \frac{1}{\gamma P_0} \quad (2)$$

In Equation 2, $L_{NL}$ denotes a nonlinear length, y denotes a nonlinear coefficient of an optical fiber, and $P_0$ denotes a peak power of an optical signal. Unlike a dispersion coefficient, there are various degrees of nonlinear coefficients of an optical fiber based on respective types of optical fibers, and thus, it is easy to set a nonlinear length of an optical fiber, as compared to a dispersion length. Second-order dispersion and self-phase modulation are basic phenomena which an optical signal undergoes as the optical signal propagates inside an optical fiber. A basic nonlinear Schrödinger Equation that corresponds to a variation in an optical signal which includes these basic phenomena may be expressed as follows:

[Equation 3]

$$j\frac{\partial A}{\partial z} = \beta_2 \frac{\partial^2 A}{\partial T^2} - \gamma |A|^2 A \quad (3)$$

In Equation 3, A denotes an envelope of an optical signal, and here the effect of attenuation is not considered. z corresponds to a proceeding direction of light inside an optical fiber, and as can be seen in Equation 3, as an optical signal proceeds by an infinitesimal displacement dz, the optical signal undergoes a second-order dispersion, which is expressed in initial term of the right side of Equation 3, and a self-phase modulation, which is expressed in second term of the right side of Equation 3.

Further, when a width of an optical signal is less than the level of ps, a significant Raman-induced frequency shift occurs, whereby a high frequency component in a spectrum of an optical signal pumps a low frequency component. A nonlinear Schrödinger Equation in which an influence due to the Raman-induced frequency shift is considered, in addition to the second-order dispersion and the self-phase modulation, may be expressed as shown in Equation 4 below:

[Equation 4]

$$j\frac{\partial A}{\partial z} = \beta_2 \frac{\partial^2 A}{\partial T^2} - \gamma\{(1-f_R)|A|^2 + f_R h_R(t) * |A|^2\}A \quad (4)$$

In Equation 4, $f_R$ denotes a fraction of Raman response which corresponds to the nonlinear polarization, and $h_R(t)$ denotes a Raman response function, and * denotes a convolution operation. In particular, as an optical signal on the level of fs propagates through an optical fiber, and, as expressed in Equation 4, the optical signal experiences complex changes on the time axis and in a frequency domain by dispersion, self-phase modulation, and Raman-induced frequency shift.

In the optical converting unit 70 of the light source system 100 according to the current exemplary embodiment, in the frequency shifting unit 71 which performs a first operation, that is, in a negative dispersion high-nonlinear optical fiber in which soliton-maintaining frequency shifting is performed, seed light undergoes a frequency shift by which a portion of seed light having a short wavelength band is shifted to a long wavelength band in a soliton state while maintaining a shape. Next, a frequency band of a corresponding soliton component is filtered by using the filter 73, in particular, by an optical fiber grating, and in the second-order dispersion unit 75 which performs a third operation, that is, in second-order dispersion of a negative dispersion low-nonlinear optical fiber, a soliton component is dispersed on the time axis, and negative chirping is applied to the soliton component. Then, in an operation of self-phase modulation of a low-dispersion high-nonlinear optical fiber by using the self-phase modulating unit 77, a portion of the negative chirping is offset and a spectrum is compressed.

Figure 2:
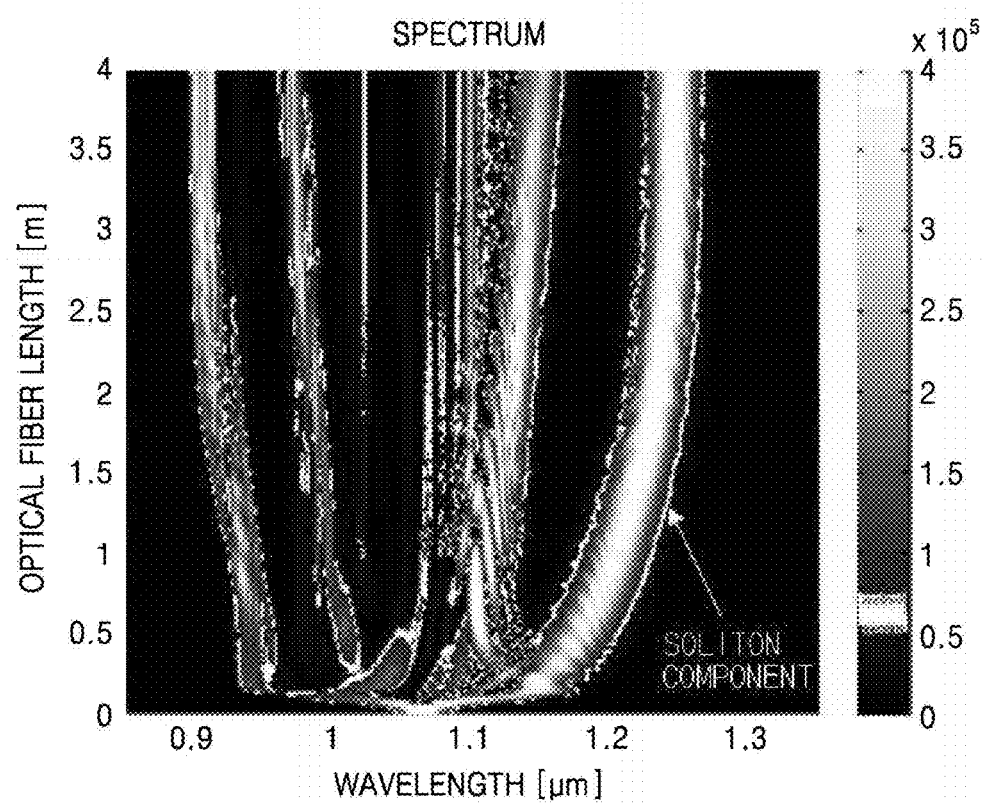
FIG. 2 illustrates an aspect of a soliton self-frequency shift.

FIG. 2 illustrates an aspect of a soliton self-frequency shift, in which an amplification signal centered at 1.064 μm is expanded on a supercontinuum, and a partial component of the amplification signal maintains a spectrum thereof, and continuously undergoes a frequency shift. FIG. 2 shows a result which may be obtained by applying a split-step Fourier method based on Equation 4 as described above.

The supercontinuum aspect largely depends on a distribution of dispersion coefficients of an optical fiber. Because a phase shift of a soliton must be offset by self-phase modulation and second-order dispersion, a dispersion coefficient of the soliton in a corresponding wavelength band must have a negative (−) sign, and when a dispersion coefficient increases toward a long wavelength band, a soliton self-frequency shift may easily occur.

Figure 3:
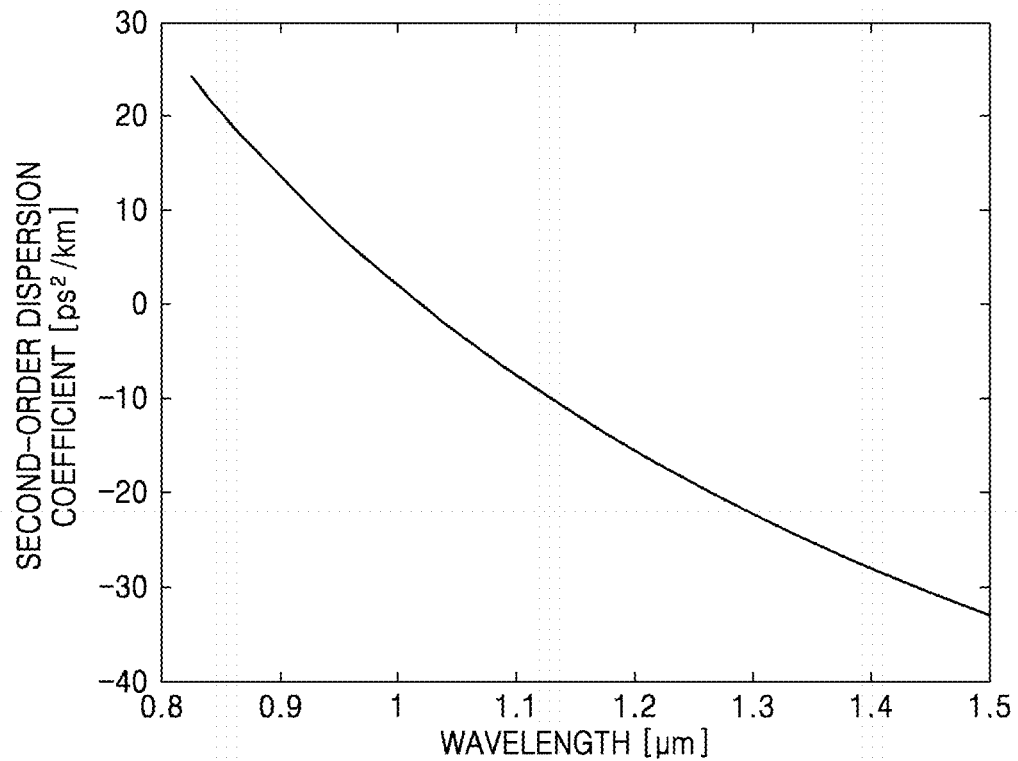
FIG. 3 illustrates a distribution of second-order dispersion coefficients of an optical fiber based on a wavelength.

FIG. 3 illustrates a distribution of second-order dispersion coefficients of an optical fiber based on a wavelength, which is an appropriate dispersion distribution to obtain an effective soliton self-frequency shift. A degree of frequency shift largely depends on an inclination of a dispersion coefficient, a nonlinear coefficient, and an intensity of seed light.

Figure 4:
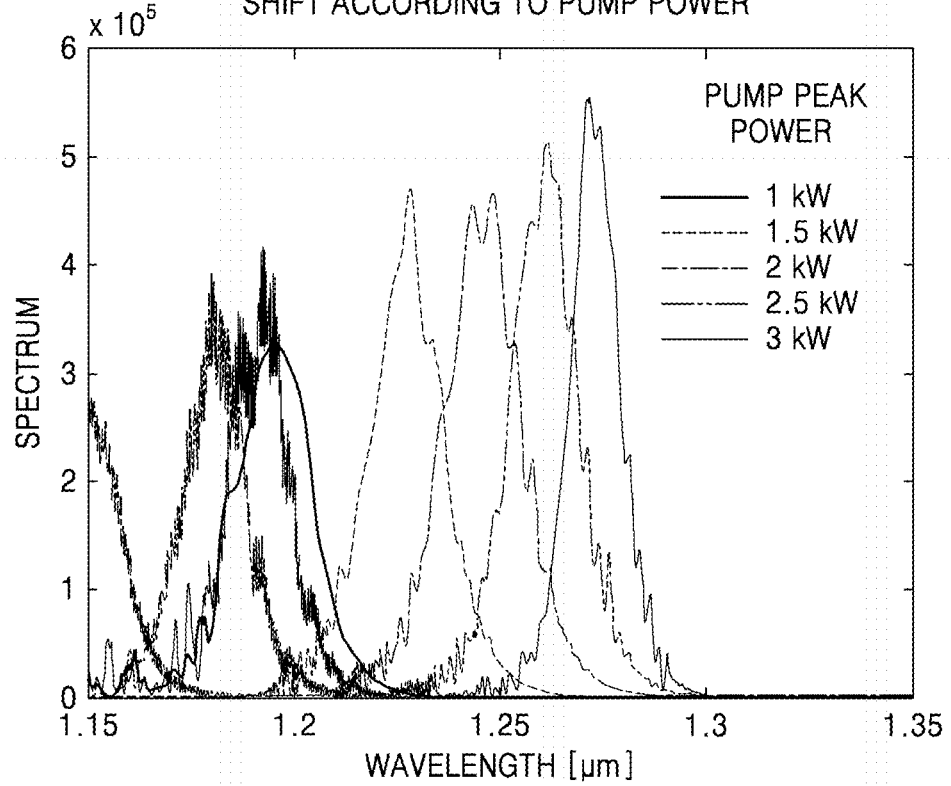
FIGS. 4 and 5 illustrate soliton self-frequency shift based on an intensity of seed light (pump power) and based on an inclination of a dispersion coefficient, respectively.
Figure 5:
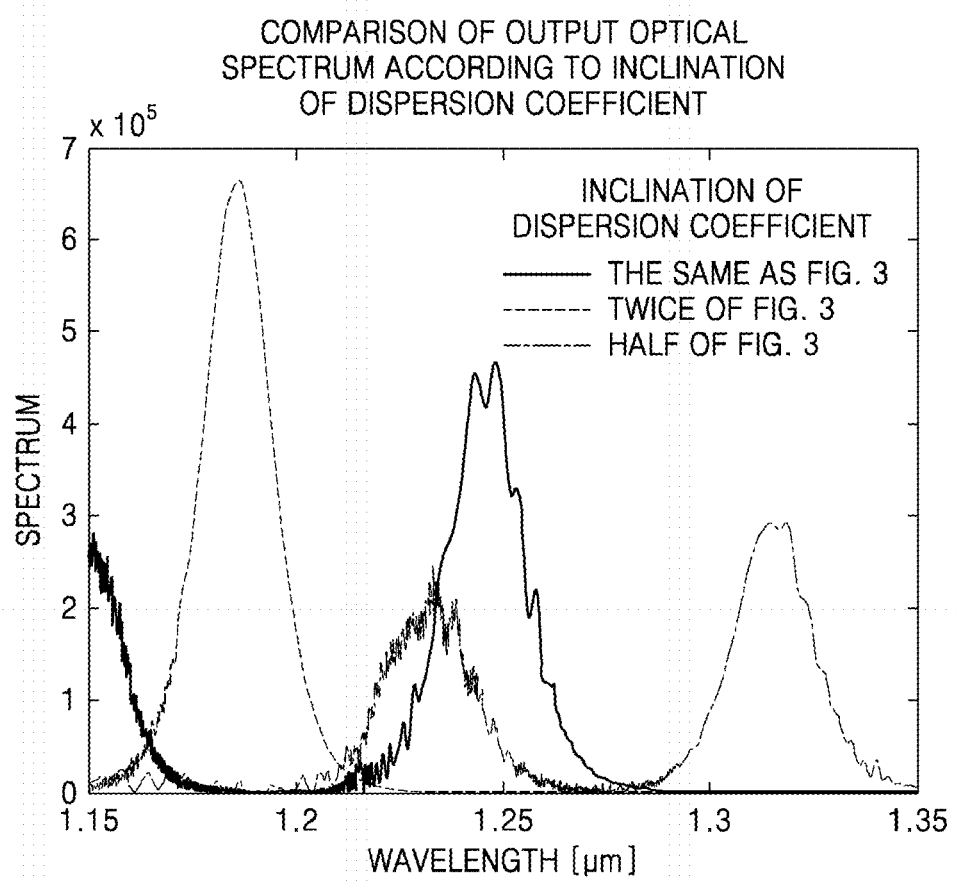

FIGS. 4 and 5 illustrate a soliton self-frequency shift based on an intensity of seed light (pump power) and an inclination of a dispersion coefficient, showing dependency as described above.

FIG. 4 shows a variation in an output spectrum based on seed light intensity under a condition as illustrated in FIG. 2, and here, it can be seen that a frequency shift is more easily generated when the seed light intensity is greater.

FIG. 5 illustrates a variation in an output spectrum based on an inclination of a dispersion coefficient with respect to a zero dispersion wavelength which is located at 1.02 μm as illustrated in FIG. 3; here, it can be seen that a frequency shift is more easily generated when a dispersion coefficient is smaller over a shifted wavelength band. Variables that are directly applied to an optical fiber, such as a nonlinear coefficient or a dispersion coefficient, are difficult to modify, and thus, a frequency shift may be induced with respect to a desired wavelength band by adjusting the pumping signal intensity.

An output optical signal at a stage of frequency shifting, which includes a frequency-shifted soliton component and occupies a relatively wide wavelength band, is appropriately filtered in a next operation so that only a frequency component in which a soliton is located remains. Even if no filtering unit is included or a filtering unit is designed to be disposed at the last position, a spectrum may be compressed in a target wavelength band. However, a frequency component of a wavelength band lower than a zero dispersion wavelength may cause cross-phase modulation in a soliton component, and arranging the filter 73 at a second stage of the optical converting unit 70 may prevent this cross phase modulation. When a filter is included in a frequency shifting optical swept light source system, a bandwidth of the filter should be set to include a band of a final swept light as described above. In order to implement the filtering function of the filter 73, an optical fiber grating may be used, and the optical fiber grating may function as a band pass filter with respect to a predetermined frequency component based on intervals of and a distribution of refractive indices of a lattice, and thus, the optical fiber grating may be used in the frequency shifting optical swept light source system 100 that is optical-fiberized, according to the current exemplary embodiment.

Figure 6B:
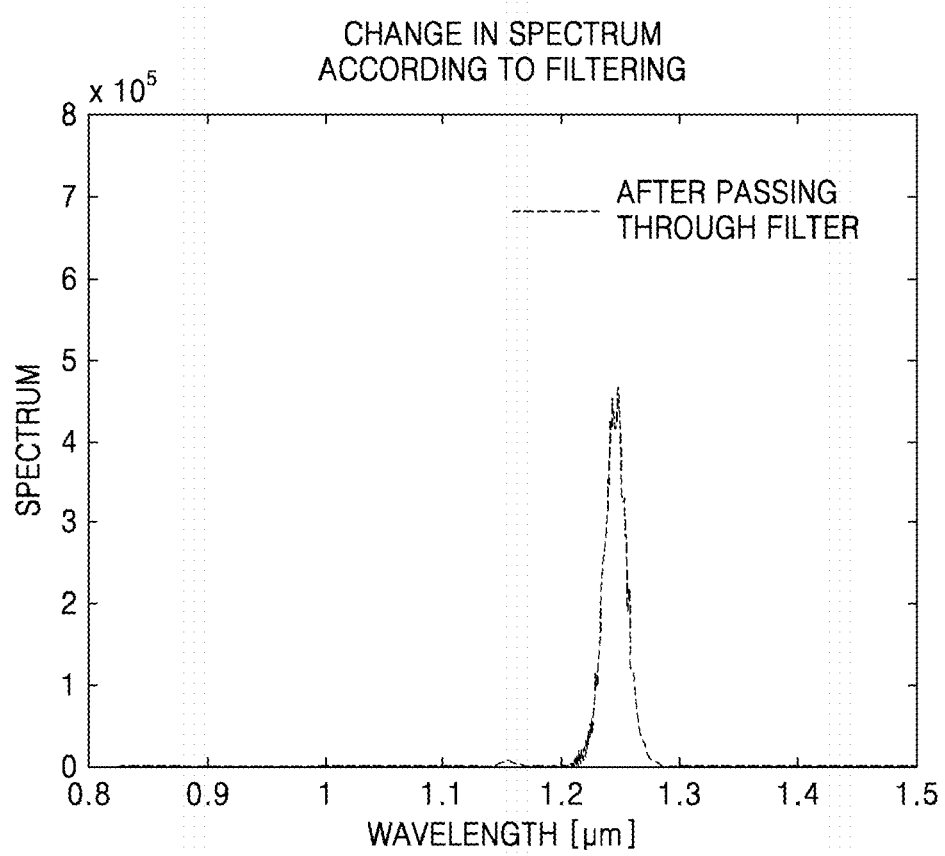
Figure 9A:
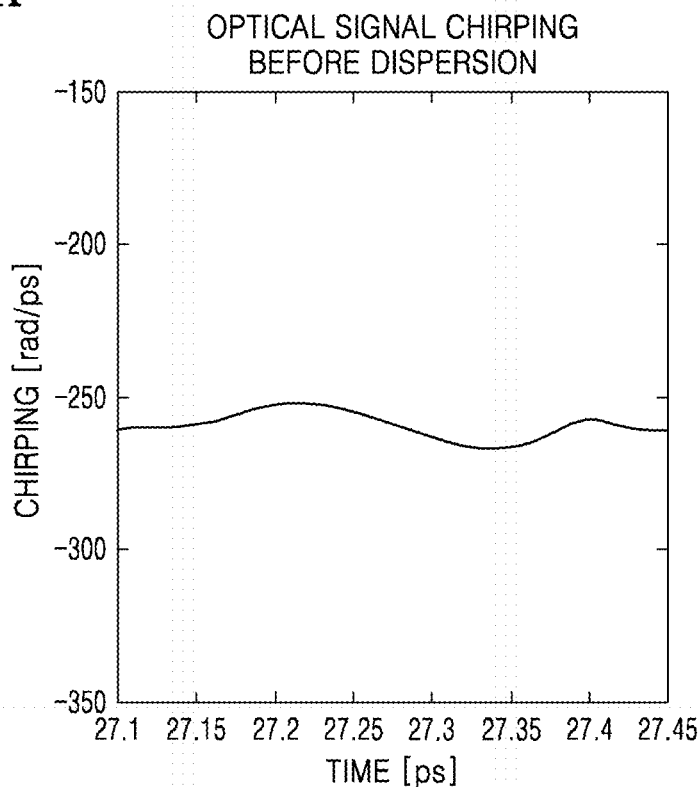
Figure 9B:
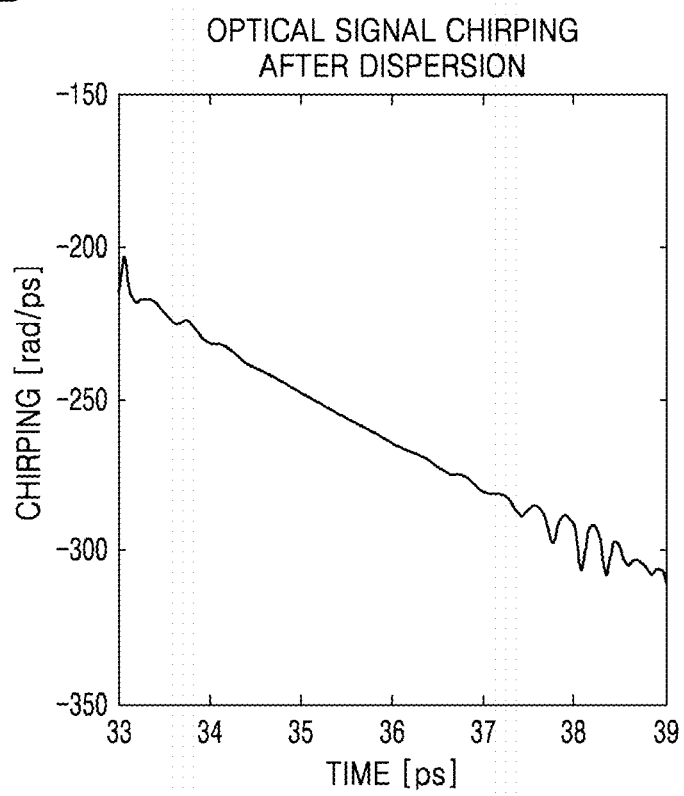
Figure 12A:
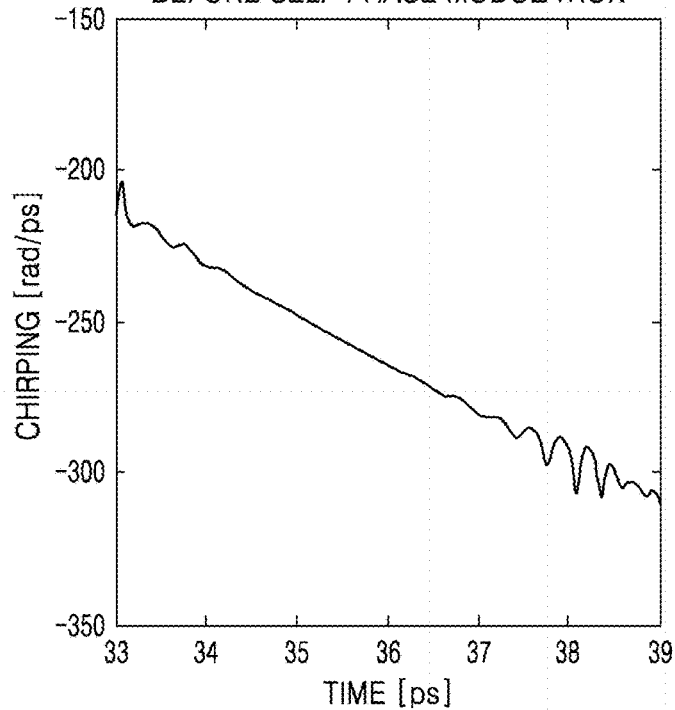
Figure 12B:
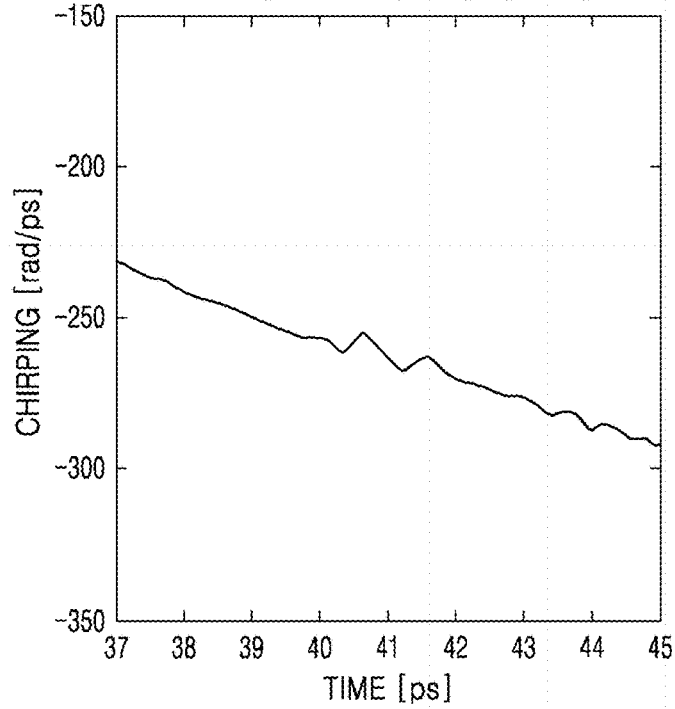

FIGS. 6A and 6B respectively illustrate the output optical signal of FIG. 2 before and after passing through the filter 73, in which a bandwidth of the filter 73 corresponds to a wavelength of approximately 80 nm.

A soliton which remains after passing through the filter 73 is a transform-limited pulse without chirping. In a third stage of the optical converting unit 70, negative chirping is applied intentionally to the soliton, and second-order dispersion of an optical fiber is used. When a nonlinear coefficient of an optical fiber is very low, the optical signal undergoes a variation which is mainly focused on second-order dispersion rather than a nonlinear effect. This may be regarded as the dispersion length, the nonlinear length, and the optical fiber length of Equations 1 and 2 satisfying Inequality 5, which is expressed below.

[Inequality 5]

$$L_{3rd} \sim L_D, L_{3rd} \langle\langle L_{NL} \quad (5)$$

In Inequality 5, a subscript "3rd" denotes an optical fiber in the third operation in the optical converting unit 70 (that is, the second-order dispersion unit 75 of the optical converting unit 70 in FIG. 1), and a sign "~" indicates a similar size degree. When the condition of Inequality 5 is satisfied and the dispersion coefficient is a negative number in a wavelength band in which a soliton is located, a spectrum of an optical signal is almost equally maintained, but an optical signal intensity is dispersed on a time axis and negative chirping is applied to the optical signal. FIGS. 7, 8, 9A, and 9B illustrate variations in an intensity and a spectrum of the optical signal and chirping on the time axis, while a soliton component which is illustrated in FIGS. 6A and 6B passes through an optical fiber. Similarly as the result shown in FIG. 2, FIGS. 7, 8, 9A, and 9B show a result which may be obtained by using the split-step Fourier method.

A portion of negative chirping which is applied by dispersion may be offset by self-phase modulation. This causes a compression of a spectrum with respect to a frequency band in which chirping is offset in a frequency domain. In order to cause a variation which is focused mainly on self-phase modulation, unlike second-order dispersion, an optical fiber having a high nonlinear coefficient and a small dispersion coefficient in a corresponding frequency band is necessary. A conditional expression which corresponds to Inequality 5 is as follows.

[Inequality 6]

$$L_{4th} \sim L_{NL}, L_{4th} \langle\langle L_D \quad (6)$$

In Inequality 6, a subscript "4th" denotes an optical fiber in a fourth stage of the optical converting unit 70 (that is, the self-phase modulating unit 77 of the optical converting unit 70 in FIG. 1). FIGS. 10, 11, 12A, and 12B illustrate variations in an intensity and a spectrum of light, and chirping on time axis due to a self phase modulation while passing through an optical fiber that satisfies Inequality 6.

As a result, the optical converting unit 70 of the light source system 100 that is optical-fiberized in the order of soliton self-frequency shift, filtering, second-order dispersion, and self phase modulation may shift a frequency range of a band of input seed light to a frequency range which corresponds to a long wavelength band and output a compressed spectrum thereof, as illustrated in FIG. 13.

In addition, because a degree of frequency shift varies based on seed light intensity as described above, a wavelength band of the output spectrum may be adjusted by varying the seed light intensity. Because the seed light intensity may be adjusted by varying a repetition rate of the amplification unit 50, the frequency shifting optical swept light source system 100 according to the current exemplary embodiment may output swept light via adjustment of a repetition rate, as illustrated in FIG. 14.

The frequency shifting optical swept light source system 100, according to the current exemplary embodiment as described above, may be used as a light source for a wavelength band other than a radiation wavelength band of a rare-earth element via compression of a spectrum that is performed after a soliton self-frequency shift in the optical converting unit 70. In addition, a position of the compressed spectrum may be adjusted by adjusting a repetition rate of seed light, and thus, the frequency shifting optical swept light source system 100 may be used as a swept light source. While light of a narrow wavelength FWHM is obtained instantaneously, because the position of the compressed spectrum is adjusted by adjusting a repetition rate of seed light, broadband light may be obtained in respect of predetermined time intervals.

For example, when YDF is used in the amplifiers 53 and 57 of the amplification unit 50 and the amplification unit 50 outputs amplified light of a band which corresponds to a wavelength of approximately 1.064 μm, in accordance with an adjustment of a repetition rate of seed light, in the optical converting unit 70, a range of swept light which is output after its frequency is shifted and then its spectrum is compressed may correspond to a range of between approximately 1100 nm and approximately 1350 nm within a range which is allowed by a pass bandwidth of the filter 73.

The frequency shifting optical swept light source system 100, according to the current exemplary embodiment as described above, may also be used in an optical measurement field as an optical-fiberized swept light source, by combining the optical converting unit 70 with the amplification unit 50 that adjusts an output optical signal intensity by adjusting a repetition rate.

Figure 15:
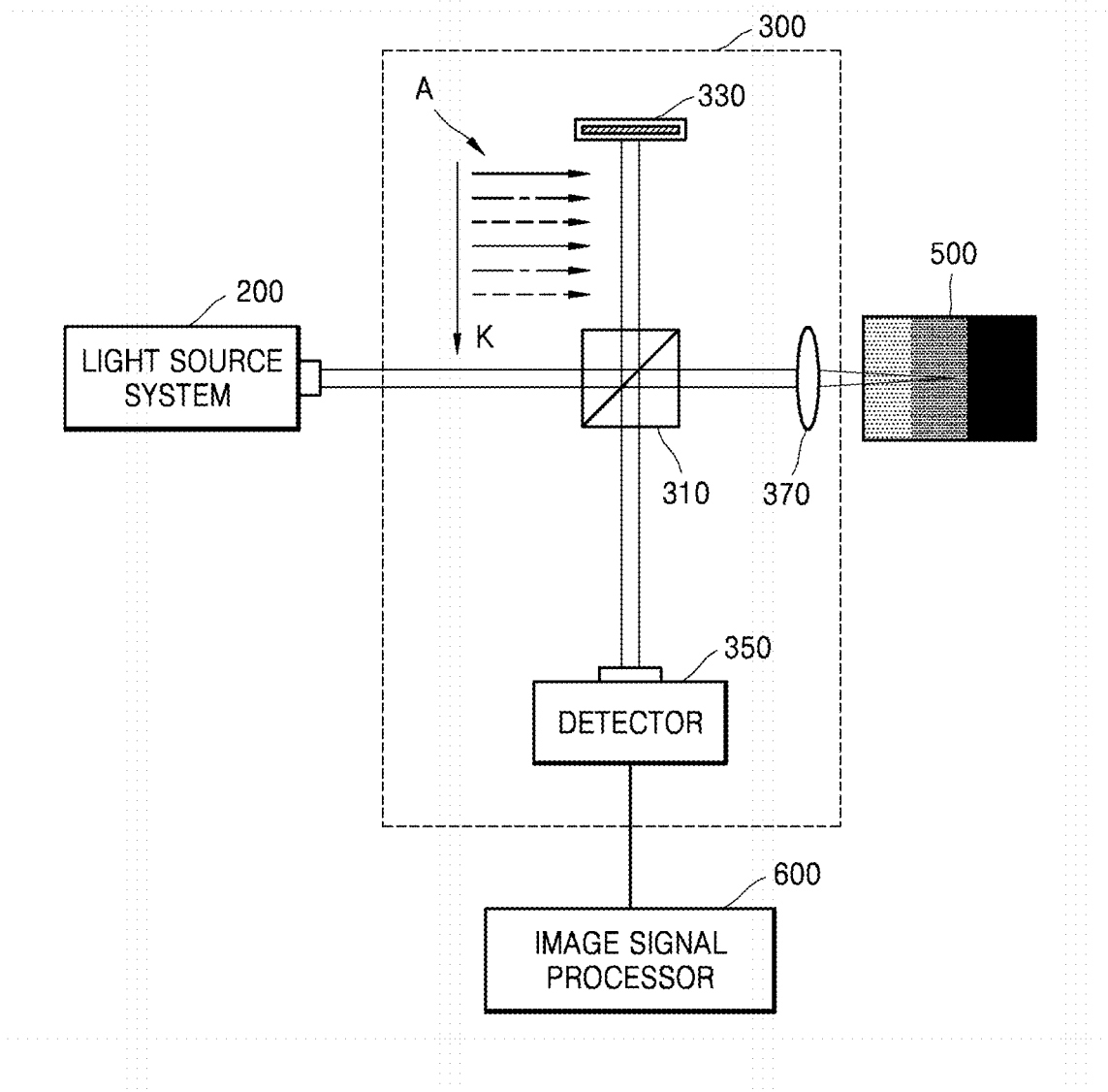
FIG. 15 is a schematic view of an optical coherence tomography apparatus as an example of an apparatus to which the frequency shifting optical swept light source system may be applied, according to an exemplary embodiment.

FIG. 15 is a schematic view of an optical coherence tomography apparatus as an example of an apparatus to which the frequency shifting optical swept light source system 100 may be applied, according to an exemplary embodiment.

Referring to FIG. 15, the optical coherence tomography apparatus may include a light source system 200, an interference optical system 300, and an image signal processor 600.

The frequency shifting optical swept light source system 100, which is described above with reference to FIG. 1 according to the current exemplary embodiment, may be used as the light source system 200. Accordingly, light that instantaneously has a narrow FWHM value but is broadband at predetermined intervals may be output. Referring to FIG. 15, "A" denotes that light output from the light source system 200 is broadband swept light that is obtained by adjusting a position of a spectrum of frequency-shifted and spectrum-compressed light based on an adjustment of a repetition rate of seed light, that is, light that is obtained by varying a frequency of the light.

The interference optical system 300 includes a beam separator 310 that separates the light output from the light source system 200 into measurement light and reference light, a reflection mirror 330 that reflects the reference light, and a detector 350 that detects an input optical signal. An object 500, from which an image signal is to be obtained, may be disposed at a side toward which the measurement light separated by using the beam separator 310 proceeds. A focusing lens 370 that focuses the measurement light on the object 500 may be further included between the beam separator 310 and the object 500.

The interference optical system 300 irradiates the measurement light, which has been separated by the beam separator 310, toward the object 500, and causes an interference between light which is reflected by the object 500 and the reference light which is reflected by the reflection mirror 330, and the detector 350 detects a result of the interference.

The image signal processor 500 generates a tomographic image of the object 500 by using an interference signal which is detected by using the detector 350.

The frequency shifting swept light source system according to one or more exemplary embodiments may be used as a light source in various fields where wavelengths other than a radiation wavelength of a rare-earth element is needed, by using compression of a spectrum that is performed after a soliton self-frequency shift. In addition, an optical-fiberized swept light source system, in which a position of the compressed spectrum is adjusted with respect to a predetermined frequency band by adjusting a repetition rate of seed light, may be implemented.

It will be understood by those of ordinary skill in the art that the exemplary embodiments described herein should be considered in a descriptive sense only and not for purposes of limitation. Descriptions of features or aspects within each exemplary embodiment should typically be considered as available for other similar features or aspects in other exemplary embodiments.

What is claimed is:

1. A frequency shifting optical swept light source system, comprising:
    a light source configured to emit light;
    an amplifier configured to amplify the light output from the light source;
    an optical converter configured to shift a frequency of the amplified light and to compress a spectrum of the amplified light; and
    a controller configured to control a current signal which is applied to the light source such that a repetition rate of the light output from the light source is adjusted, so that an intensity of the amplified light is adjusted, in order to thereby adjust a position of the compressed spectrum with respect to a first predetermined frequency band.

2. The frequency shifting optical swept light source system of claim 1, wherein the optical converter comprises:
    a frequency shifter configured to shift a first wavelength range of a band of the amplified light to a second wavelength range;
    a second-order disperser configured to disperse light processed by the frequency shifter, on a time axis; and
    a self phase modulator configured to compress a spectrum of the light received from the second-order disperser.

3. The frequency shifting optical swept light source system of claim 2, wherein the frequency shifter is further configured to perform soliton self-frequency shifting.

4. The frequency shifting optical swept light source system of claim 3, wherein the frequency shifter includes a negative dispersion high-nonlinear optical fiber.

5. The frequency shifting optical swept light source system of claim 2, wherein the second-order disperser is further configured to perform second-order dispersion.

6. The frequency shifting optical swept light source system of claim 5, wherein the second-order disperser includes a negative dispersion low-nonlinear optical fiber.

7. The frequency shifting optical swept light source system of claim 2, wherein the self phase modulator comprises a low-dispersion high-nonlinear optical fiber.

8. The frequency shifting optical swept light source system of claim 2, wherein the optical converter further comprises a filter that is disposed between the frequency shifter and the second-order disperser or between the second-order disperser and the self phase modulator, the filter being configured to pass a second predetermined frequency band.

9. The frequency shifting optical swept light source system of claim 8, wherein the filter comprises an optical fiber grating configured to function as a band pass filter with respect to a predetermined frequency component.

10. The frequency shifting optical swept light source system of claim 1, wherein the optical converter comprises:
    a soliton self-frequency shifter configured to perform frequency shifting in a soliton state, such that a first wavelength range of a band of the amplified light is shifted to a second wavelength range;
    a second-order disperser configured to disperse a soliton component which is incident from the soliton self-frequency shifter on a time axis and to apply negative chirping to the soliton component; and
    a self phase modulator configured to offset a portion of the negative chirping applied by using the second-order disperser, via self phase modulation, so as to cause spectrum compression with respect to the frequency band for which the portion of the negative chirping is offset, in a frequency domain.

11. The frequency shifting optical swept light source system of claim 10, wherein the optical converter further comprises a filter that is disposed between the soliton self-frequency shifter and the second-order disperser, the filter being configured to pass a predetermined frequency band of the soliton component.

12. The frequency shifting optical swept light source system of claim 11, wherein the filter comprises an optical fiber grating configured to function as a band pass filter with respect to a predetermined frequency component.

13. The frequency shifting optical swept light source system of claim 10, wherein the soliton self-frequency shifter includes a negative dispersion high-nonlinear optical fiber.

14. The frequency shifting optical swept light source system of claim 10, wherein the second-order disperser includes a negative dispersion low-nonlinear optical fiber.

15. The frequency shifting optical swept light source system of claim 10, wherein the self phase modulator includes a low-dispersion high-nonlinear optical fiber.

16. The frequency shifting optical swept light source system of claim 1, wherein the amplifier is structured to perform at least a double amplification.

17. An optical coherence tomography apparatus comprising:
    a broadband swept light source system configured to implement the frequency shifting optical swept light source system of claim 1;

an interference optical system configured to separate light which is output from the frequency shifting optical swept light source system of claim 1 into measurement light and reference light, to irradiate the measurement light toward an object, and to cause an interference between light reflected by the object and the reference light in order to detect an interference signal; and an image signal processor configured to generate a tomographic image of the object by using the detected interference signal.

18. The optical coherence tomography apparatus of claim 17, wherein the amplifier of the frequency shifting optical swept light source system of claim 1 is structured to perform at least a double amplification.

19. A method for performing frequency shifting and amplification to light, comprising:

receiving light emitted from a light source;

amplifying the received light;

shifting a frequency of the amplified light;

compressing a spectrum of the frequency-shifted amplified light; and controlling a current signal which is applied to the light source such that a repetition rate of the light output from the light source is adjusted, so that an intensity of the amplified light is adjusted, in order to thereby adjust a position of the compressed spectrum with respect to a first predetermined frequency band.

20. The method of claim 19, wherein the shifting the frequency comprises shifting a first wavelength range of a band of the amplified light to a second wavelength range, and wherein the compressing the spectrum comprises dispersing the frequency-shifted amplified light on a time axis and compressing a spectrum of a result of the dispersing.

* * * * *